(12) United States Patent
Adey (10) Patent No.: US 7,235,400 B2
(45) Date of Patent: Jun. 26, 2007

(54) LAMINATED MICROARRAY INTERFACE DEVICE

(75) Inventor: Nils B. Adey, Salt Lake City, UT (US)

(73) Assignee: BioMicro Systems, Inc., Salt Lake City, UT (US)

( * ) Notice: Subject to any disclaimer, the term of this patent is extended or adjusted under 35 U.S.C. 154(b) by 527 days.

(21) Appl. No.: 10/211,503

(22) Filed: Aug. 2, 2002

(65) Prior Publication Data

US 2002/0192701 A1    Dec. 19, 2002

Related U.S. Application Data

(63) Continuation-in-part of application No. PCT/US02/07113, filed on Mar. 8, 2002.

(60) Provisional application No. 60/339,851, filed on Dec. 12, 2001, provisional application No. 60/313,703, filed on Aug. 20, 2001, provisional application No. 60/284,427, filed on Apr. 17, 2001, provisional application No. 60/274,389, filed on Mar. 9, 2001.

(51) Int. Cl.
  *C12M 1/34* (2006.01)
(52) U.S. Cl. .............................. 435/287.2; 435/288.3; 435/288.4; 435/288.5; 435/293.1; 422/60; 422/102
(58) Field of Classification Search ............ 435/287.2, 435/293.1
See application file for complete search history.

(56) References Cited

U.S. PATENT DOCUMENTS

| | | | |
|---|---|---|---|
| 3,726,764 A | 4/1973 | White | 195/127 |
| 3,745,091 A | 7/1973 | McCormick | 195/139 |
| 3,879,106 A | 4/1975 | McCormick | 350/95 |
| 3,891,327 A | 6/1975 | Welch | 356/244 |
| 4,171,866 A | 10/1979 | Tolles | 350/95 |
| 4,426,451 A | 1/1984 | Columbus | |
| 4,441,793 A | 4/1984 | Elkins | 350/536 |
| 4,447,140 A | 5/1984 | Campbell et al. | 350/534 |

(Continued)

FOREIGN PATENT DOCUMENTS

EP          0843169          5/1998

(Continued)

OTHER PUBLICATIONS

Anderson et al., "Advances in Integrated Genetic Analysis", Micro total analysis systems, Harrison and van den Berg (eds) Kluwer Academic Publishers, Dordrecht, The Netherlands, 1998, pp. 11-16.

(Continued)

*Primary Examiner*—William H. Beisner
(74) *Attorney, Agent, or Firm*—Brinks Hofer Gilson & Lione (57) ABSTRACT

A device for forming a low volume reaction chamber on a substrate such as a microarray slide and its method of use is disclosed. The reaction chamber forming device has an adhesive laminate design that permits it to be manufactured as a disposable device. A preferred embodiment of the device includes pneumatically actuatable mixing bladders, which can be inflated or deflated to produce deflection of a wall of the reaction chamber in and out with respect to the reaction chamber to generate movement and mixing of fluid within the reaction chamber.

44 Claims, 8 Drawing Sheets

U.S. PATENT DOCUMENTS

| | | | |
|---|---|---|---|
| 4,494,912 A | 1/1985 | Pauliukonis | 417/347 |
| 4,505,557 A | 3/1985 | Golias | 350/536 |
| 4,526,690 A | 7/1985 | Kiovsky et al. | 210/335 |
| 4,687,423 A | 8/1987 | Maget et al. | 417/379 |
| 4,722,598 A | 2/1988 | Ford | 350/536 |
| 4,790,640 A | 12/1988 | Nason | 350/534 |
| 4,853,262 A | 8/1989 | Horie et al. | 428/13 |
| 4,908,319 A | 3/1990 | Smyczek et al. | 435/285 |
| 4,911,782 A | 3/1990 | Brown | 156/633 |
| 4,948,564 A | 8/1990 | Root et al. | 422/101 |
| 4,985,206 A | 1/1991 | Bowman et al. | 422/99 |
| 5,023,187 A | 6/1991 | Koebler et al. | 436/180 |
| RE33,826 E | 2/1992 | Mitchell | 359/398 |
| 5,100,626 A | 3/1992 | Levin | 422/100 |
| 5,100,775 A | 3/1992 | Smyczek et al. | 435/6 |
| 5,192,503 A | 3/1993 | McGrath et al. | 422/57 |
| 5,200,152 A | 4/1993 | Brown | 422/102 |
| 5,273,905 A | 12/1993 | Muller et al. | 435/301 |
| 5,313,264 A | 5/1994 | Ivarsson et al. | 356/73 |
| 5,346,672 A | 9/1994 | Stapleton et al. | 422/102 |
| 5,360,741 A | 11/1994 | Hunnell | 435/290 |
| 5,364,790 A | 11/1994 | Atwood et al. | 435/288 |
| 5,393,494 A | 2/1995 | Greenfield et al. | 422/68 |
| 5,417,576 A | 5/1995 | Hill | 435/299 |
| 5,443,890 A | 8/1995 | Ohman | 428/167 |
| 5,460,945 A | 10/1995 | Springer et al. | 435/7.24 |
| 5,466,603 A | 11/1995 | Meehan et al. | 435/285.1 |
| 5,503,803 A | 4/1996 | Brown | 422/102 |
| 5,518,925 A | 5/1996 | Tyndorf et al. | 435/305.2 |
| 5,527,510 A | 6/1996 | Atwood et al. | 422/104 |
| 5,571,721 A | 11/1996 | Turner | 435/305.1 |
| 5,578,270 A | 11/1996 | Reichler et al. | 422/67 |
| 5,605,813 A | 2/1997 | Stevens et al. | 435/40.52 |
| 5,637,469 A | 6/1997 | Wilding et al. | 435/7.21 |
| 5,639,428 A * | 6/1997 | Cottingham | 422/112 |
| 5,658,723 A | 8/1997 | Oberhardt | 435/4 |
| 5,661,029 A | 8/1997 | Self et al. | 435/288.3 |
| 5,675,700 A | 10/1997 | Atwood et al. | 392/382 |
| 5,681,741 A | 10/1997 | Atwood et al. | 435/287.2 |
| 5,718,567 A | 2/1998 | Rapp et al. | 417/395 |
| 5,726,026 A | 3/1998 | Wilding et al. | 435/7.21 |
| 5,846,727 A | 12/1998 | Soper et al. | 435/6 |
| 5,856,174 A | 1/1999 | Lipshutz et al. | 435/286.5 |
| 5,866,345 A | 2/1999 | Wilding et al. | 435/7.21 |
| 5,876,675 A | 3/1999 | Kennedy | 422/99 |
| 5,902,096 A | 5/1999 | Behringer et al. | 417/395 |
| 5,922,591 A | 7/1999 | Anderson et al. | 435/287.2 |
| 5,922,604 A | 7/1999 | Stapleton et al. | 436/46 |
| 5,928,880 A | 7/1999 | Wilding et al. | 435/7.21 |
| 5,935,524 A | 8/1999 | Bass et al. | 422/104 |
| 5,948,673 A * | 9/1999 | Cottingham | 435/287.2 |
| 5,955,028 A | 9/1999 | Chow | 422/63 |
| 5,958,341 A | 9/1999 | Chu | 422/99 |
| 5,958,760 A | 9/1999 | Freeman | 435/286.5 |
| 5,989,402 A | 11/1999 | Chow et al. | 204/601 |
| 5,989,499 A | 11/1999 | Catanzariti | 422/63 |
| 6,008,893 A | 12/1999 | Roos et al. | 356/246 |
| 6,020,187 A | 2/2000 | Tam | 435/287.2 |
| 6,033,544 A | 3/2000 | Demers et al. | 204/450 |
| 6,033,628 A | 3/2000 | Kaltenbach et al. | 422/68.1 |
| 6,037,168 A | 3/2000 | Brown | 435/288.3 |
| 6,043,080 A | 3/2000 | Lipshutz et al. | 435/287.2 |
| 6,048,498 A | 4/2000 | Kennedy | 422/99 |
| 6,052,224 A | 4/2000 | Richardson | 359/398 |
| 6,054,277 A | 4/2000 | Furcht et al. | 435/6 |
| 6,057,100 A | 5/2000 | Heyneker | 435/6 |
| 6,063,579 A | 5/2000 | Bevirt | 435/6 |
| 6,071,478 A | 6/2000 | Chow | 422/81 |
| 6,074,725 A | 6/2000 | Kennedy | 428/188 |
| 6,074,827 A | 6/2000 | Nelson et al. | 435/6 |
| 6,083,763 A | 7/2000 | Balch | 436/518 |
| 6,103,199 A | 8/2000 | Bjornson et al. | 422/100 |
| 6,114,122 A | 9/2000 | Besemer et al. | 435/6 |
| 6,130,098 A | 10/2000 | Handique et al. | 436/180 |
| 6,132,685 A | 10/2000 | Kercso et al. | 422/104 |
| 6,136,592 A | 10/2000 | Leighton | 435/288 |
| 6,140,044 A | 10/2000 | Besemer et al. | 435/6 |
| 6,143,496 A | 11/2000 | Brown et al. | 435/6 |
| 6,144,447 A | 11/2000 | Ohman et al. | 356/246 |
| 6,158,712 A | 12/2000 | Craig | 251/61.1 |
| 6,159,727 A | 12/2000 | Bochkariov | 435/287.2 |
| 6,167,910 B1 | 1/2001 | Chow | 137/827 |
| 6,168,948 B1 | 1/2001 | Anderson et al. | 435/287.2 |
| 6,197,494 B1 | 3/2001 | Oberhardt | 435/4 |
| 6,197,595 B1 | 3/2001 | Anderson et al. | 436/180 |
| 6,200,814 B1 | 3/2001 | Malmqvist et al. | 436/52 |
| 6,207,031 B1 | 3/2001 | Adourian et al. | 204/451 |
| 6,225,059 B1 | 5/2001 | Ackley et al. | 435/6 |
| 6,225,109 B1 | 5/2001 | Juncosa et al. | 435/288.5 |
| 6,238,910 B1 | 5/2001 | Custance et al. | 435/287.2 |
| 6,251,343 B1 | 6/2001 | Dubrow et al. | 422/102 |
| 6,251,601 B1 | 6/2001 | Bao et al. | 435/6 |
| 6,268,219 B1 | 7/2001 | McBride et al. | 436/180 |
| 6,272,939 B1 | 8/2001 | Frye et al. | 73/864.81 |
| 6,274,337 B1 | 8/2001 | Parce et al. | 435/29 |
| 6,284,113 B1 | 9/2001 | Bjornson et al. | 204/453 |
| 6,284,525 B1 | 9/2001 | Mathies et al. | 435/287.2 |
| 6,284,531 B1 | 9/2001 | Zhu et al. | 435/305.3 |
| 6,287,850 B1 | 9/2001 | Besemer et al. | 435/287.2 |
| 6,303,288 B1 | 10/2001 | Furcht et al. | 435/4 |
| 6,303,389 B1 | 10/2001 | Levin et al. | 436/518 |
| 6,309,875 B1 | 10/2001 | Gordon | 435/287.2 |
| 6,326,211 B1 | 12/2001 | Anderson et al. | 436/177 |
| 6,376,256 B1 | 4/2002 | Dunnington et al. | 436/178 |
| 6,399,394 B1 | 6/2002 | Dahm et al. | 436/180 |
| 6,555,361 B1 * | 4/2003 | Lyman et al. | 435/287.2 |
| 6,569,674 B1 * | 5/2003 | McGarry et al. | 435/287.2 |
| 2001/0003652 A1 | 6/2001 | Freeman | 435/286.5 |
| 2001/0018183 A1 | 8/2001 | Bao et al. | 435/6 |
| 2002/0022261 A1 | 2/2002 | Anderson et al. | 435/287.2 |
| 2002/0071339 A1 | 6/2002 | Winkler et al. | 366/144 |
| 2002/0074271 A1 | 6/2002 | Hu et al. | 210/101 |
| 2002/0127146 A1 | 9/2002 | Bergh et al. | 422/89 |
| 2004/0037739 A1 * | 2/2004 | McNeely et al. | 422/58 |
| 2005/0019898 A1 * | 1/2005 | Adey et al. | 435/286.7 |

FOREIGN PATENT DOCUMENTS

| | | |
|---|---|---|
| WO | WO90/05295 | 5/1990 |
| WO | WO90/05305 | 5/1990 |
| WO | WO94/23326 | 10/1994 |
| WO | WO99/36766 | 7/1999 |
| WO | WO00/38838 | 7/2000 |
| WO | WO00/63670 | 10/2000 |
| WO | WO01/04634 | 1/2001 |
| WO | WO01/25137 | 4/2001 |
| WO | WO01/25138 | 4/2001 |
| WO | WO01/41931 | 6/2001 |
| WO | WO01/43871 | 6/2001 |
| WO | WO01/68257 | 9/2001 |
| WO | WO01/70381 | 9/2001 |
| WO | WO01/70400 | 9/2001 |
| WO | WO01/78893 | 10/2001 |
| WO | WO01/89695 | 11/2001 |
| WO | WO01/89787 | 11/2001 |
| WO | WO01/89788 | 11/2001 |
| WO | WO01/94635 | 12/2001 |
| WO | WO02/18756 | 3/2002 |
| WO | WO02/18785 | 3/2002 |

| | | |
|---|---|---|
| WO | WO02/18949 | 3/2002 |

OTHER PUBLICATIONS

Anderson et al., "Fabrication of Topologically Complex Three-Dimensional Microfluidic Systems in PDMS by Rapid Prototyping," Analytical Chemistry, vol. 72, No. 14, Jul. 15, 2000, pp. 3158-3164.

Anderson et al., "Microfluidic Biochemical Analysis System," Transducers '97 1997 International Conference on Solid-State Sensor and Acutautors, Chicago, Jun. 16-19, 1997, pp. 477-480.

Henze, Microarrays, BioForum vol. 5, Feb. 1, 2001.

Jo et al., "Fabrication of Three-Dimensinal Microfluidic Systems by Stacking Molded Polydimethylsiloxane (PDMS) Layers," SPIE Conf. On Microfluidic Devices and Systems II, Sep. 1999, Santa Clara CA, SPIE vol. 3877, pp. 222-229.

Man et al., "Microfluidic Plastic Capillaries on Silicon Substrates: A New Inexpensive Technology for Bioanalysis Chips," 10th Annual IEEE MEMS Workshop, 1997, pp. 311-316.

Mitchell, Peter, "Microfluidic-Downsizing Large Scale Biology," Nature Biotechnology, vol. 19, Aug. 2001, pp. 717-721.

Unger et al., "Monolithic Microfabricated Valves and Pumps by Multilayer Soft Lithography," Science, vol. 288, Apr. 7, 2000, pp. 113-116.

Wego et al., "A self-filling micropump based on PCB technology," Sensors and Actuators A 88 (2001), pp. 220-226.

Information on Clontech Atlas™ ™ Glass Hybridization Chambers, CLONTECHniques, Jan. 2000.

Information on Corning CMT™ ™ Hybridization Chamber from Corning web site and package inserts, no date provided.

Information on Grace Biolabs Hybridization Chambers from www.gracebio.com, printed Nov. 26, 2001.

Information on Schleicher and Schuell FAST™ ™ Slides, from www.s-and-s.com, printed Jan. 9, 2002.

Information on Schleicher and Schuell CAST™ ™ Slides from www.s-and-s.com, printed Jan. 9, 2002.

Information on TeleChem International, Inc., ArrayIt™ ™ Hybridization Cassette, from www.arrayit.com, printed Mar. 30, 2002.

Information on Thermo Hybaid EasiSeal, www.thermohybaid.com, printed Nov. 9, 2001.

* cited by examiner

LAMINATED MICROARRAY INTERFACE DEVICE

RELATED APPLICATIONS

This application is a continuation-in-part of PCT international application number PCT/US02/07113, filed Mar. 8, 2002, which application claims the benefit of U.S. Provisional Application No. 60/274,389, filed Mar. 9, 2001, U.S. Provisional Application No. 60/284,427, filed Apr. 17, 2001, U.S. Provisional Application No. 60/313,703, filed Aug. 20, 2001, and U.S. Provisional Application No. 60/339,851, filed Dec. 12, 2001.

BACKGROUND

A variety of biological and chemical assays have been developed for detecting the presence of compounds of interest in samples. In the biomedical field, methods for detecting the presence of specific nucleotide sequences, proteins or peptides are utilized, for example, in diagnosing various medical conditions, determining predisposition of patients to diseases, and performing DNA fingerprinting.

In general, biological and chemical assays are based on exposing an unknown sample to one or more known reactants and monitoring the progress or measuring the outcome of the reaction. It is often desirable to expose a sample to multiple reactants, to react multiple dilutions of a single sample with one or multiple reactants, to expose multiple samples to a single reactant, or to perform multiple repetitions of a particular assay for a given sample, in order to improve reliability. There is currently a high level of interest in the development of high throughput methods for performing multiple biological and chemical analyses of this type simultaneously, quickly, and conveniently.

One recently developed method for performing multiple chemical reactions simultaneously is to form a microarray of multiple spots of reactant molecules on a planar substrate such as a glass microscope slide, typically in a two-dimensional grid pattern, and apply liquid reagents and reactants to the slide to contact multiple spots simultaneously. Various reaction steps may be performed with the bound molecules in the microarray, including exposure of bound reactant molecules to liquid reagents or reactants, washing, and incubation steps. The progress or outcome of the reaction may be monitored at each spot in the microarray in order to characterize either material(s) immobilized on the slide or material(s) in a liquid sample. Although it is typical to immobilize known reactants on the substrate and expose an unknown liquid sample to the immobilized reactants and monitor the reaction between the sample and the various reactants in order to characterize the sample, it is also possible to immobilize one or more unknown samples on the substrate and expose them to a liquid containing one or more known reactants.

Microarrays are frequently used in analysis of DNA samples, but may also be used in diagnostic testing of other types of patient samples. Spots in microarrays may be formed of various large biomolecules, such as DNA, RNA, and proteins; smaller molecules such as drugs; co-factors, signaling molecules, peptides or oligonucleotides. Cultured cells may also be grown onto microarrays. For example, if it is desired to analyze gene expression by studying the presence of particular DNA sequences in a patient sample, the sample is exposed to a microarray of spots formed of oligonucleotides having sequences complementary to sequences of interest. If the DNA sequence of interest is present in a patient sample, it will hybridize with the bound oligonucleotides. The occurrence of hybridization at a particular spot then indicates the presence, and perhaps additionally the quantity, of the sequence associated with that spot in the sample. Hybridization can be detected by various methods. One commonly used method involves labeling the sample with a fluorescent dye, so that fluorescence can be detected at spots where hybridization occurred. Various types of slide readers are commercially available for reading microarray slides.

Microarrays offer great potential for performing complex analyses of samples by carrying out multiple detection reactions simultaneously. However, a current limitation of microarrays is the time and care required to process slides to obtain reliably high quality results. The need for high quality processing is particularly pronounced because individual microarrays slides are expensive and only limited quantities of the samples used in the reactions may be available, making it particularly important to obtain good results consistently.

Both manual and automated methods of performing microarray hybridizations have been developed. However, to date, no method has been completely satisfactory. In order to process a microarray manually, reagents or reactant solutions are applied to the microarray slide and a cover slip applied to spread the solution out into a thin layer that covers the entire microarray and prevents evaporation. Evaporation of solution and non-uniformity of the fluid layer are problematic. Moreover, the success of the procedure is largely dependent on the skill of the human technician. In addition, the hybridization fluid is static, which can limit sensitivity.

Various methods have been developed to overcome the limitations of manual slide processing. These range from simple slide processing chambers designed to simplify the application of solutions to microarray slides and reduce loss and leakage of solutions, to large and expensive machines capable of processing large numbers of slides simultaneously.

Loeffler et al. (PCT publication WO 00/63670, dated Oct. 26, 2000) describe a slide processing chamber designed for processing microarray slides. Freeman (U.S. Pat. No. 5,958,760, issued Sep. 28, 1999), Stapleton et al. (U.S. Pat. No. 5,922,604 issued Jul. 13, 1999), Stevens et al. (U.S. Pat. No. 5,605,813, issued Feb. 25, 1997) and Richardson (U.S. Pat. No. 6,052,224, issued Apr. 18, 2000) all disclose slide processing chambers not specifically disclosed for use in microarray processing, which however serve to illustrate the general state of the art relating to the processing of individual slides.

Devices capable of processing multiple slides simultaneously in an automated fashion are described by Custance (U.S. Pat. No. 6,238,910, issued May 29, 2001) and Juncosa et al. (U.S. Pat. No. 6,225,109, issued May 1, 2001).

All of the above mentioned patents or applications are incorporated herein by reference.

Devices for automated processing of microarray slides offer advantages in terms of reproducibility and ability to process large numbers of slides, but require relatively large sample volumes and are prohibitively expensive for labs that do not need to process large numbers of slides. Although reproducibility is significantly improved by automation, the results obtained with commercially available instruments may be of lower quality than those obtained with manual processing.

In many applications, it is desirable to mix or agitate fluid on the surface of the microarray during processing. In particular, if the microarray is used to detect materials that occur in low concentrations in the liquid sample, the amount of time needed for molecules in the liquid sample to diffuse to binding locations on the microarray may be a limiting factor. Some slide processing systems incorporate mixing functions but effective mixing in low volume hybridization chambers is difficult to attain.

SUMMARY OF THE INVENTION

The present invention is a microarray interface device that can be connected to a substrate bearing a microarray of spots made up of DNA, RNA, oligonucleotides, proteins, or other biomolecules and can provide continuous mixing of sample solutions in contact with the microarray. Applicants' earlier invention disclosures of various methods and systems for microfluidic interfacing to arrays set forth in U.S. provisional patent application Nos. 60/274,389, 60/284,427, and 60/313,703 are incorporated herein.

The novel microarray interface device is an adhesive laminate device formed of multiple thin layers, as will be described subsequently, and is a relatively flexible structure. It has the advantage of being simple and inexpensive to manufacture. It also has a low thermal mass which allows it to be brought rapidly to a desired reaction temperature.

The array interface devices described herein may be adapted to perform hybridizations on conventional 1"×3" microarray slides. They may also be readily adapted to a variety of different microarray formats. The devices may be adapted for use with various types of slides having different dimensions and slide surfaces. Although it is presently preferred that the slide surface be planar, the flexible nature of the device allows it to conform to curved surfaces.

STRUCTURE OF MICROARRAY INTERFACE DEVICE

Figure 1:
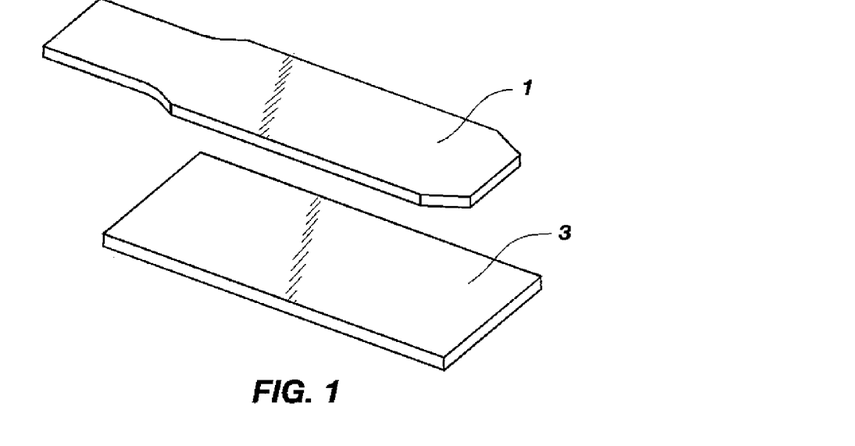
FIG. 1 depicts the assembled device before attachment to a microarray slide.

FIG. 1 illustrates the assembled microarray interface device 1. Device 1 is capable of binding to a substrate, such as a glass microarray slide 3, to form a sealed reaction chamber. Note that while the chamber is referred to as a reaction chamber, for the reason that most often a chemical reaction will be carried out within the chamber, the chamber is not limited to chemical reactions. Other chemical associations, interactions, or fluid processing steps may take place within what will hereafter be referred to as a reaction chamber. The device may also be referred to as a reaction chamber forming device or hybridization chamber forming device. It is contemplated that the slide may be a microarray slide, a histology slide, a cytology slide, or any slide formed of glass or other material bearing biological or chemical samples of various types. Moreover, the substrate need not be a slide, but may be any other surface capable of being sealed to device 1 such that a region that is to be subjected to processing will be contained within the chamber thus formed.

Figure 2:
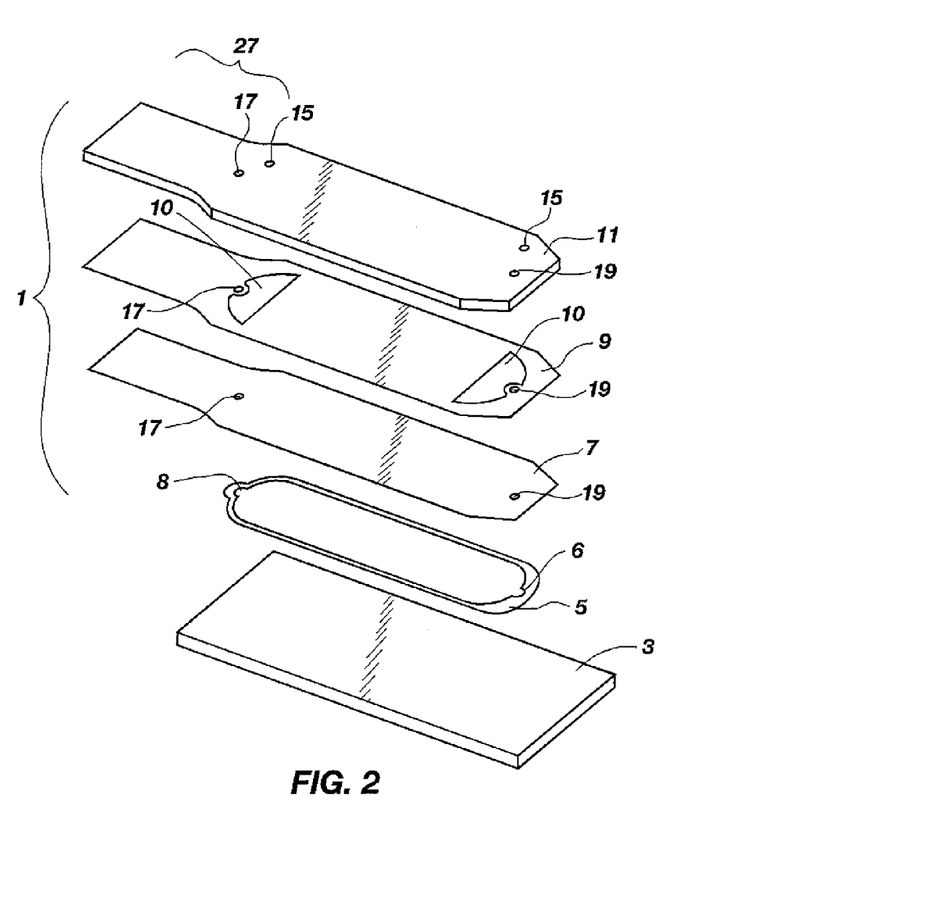
FIG. 2 is an exploded view of an embodiment of the device.
Figure 3:
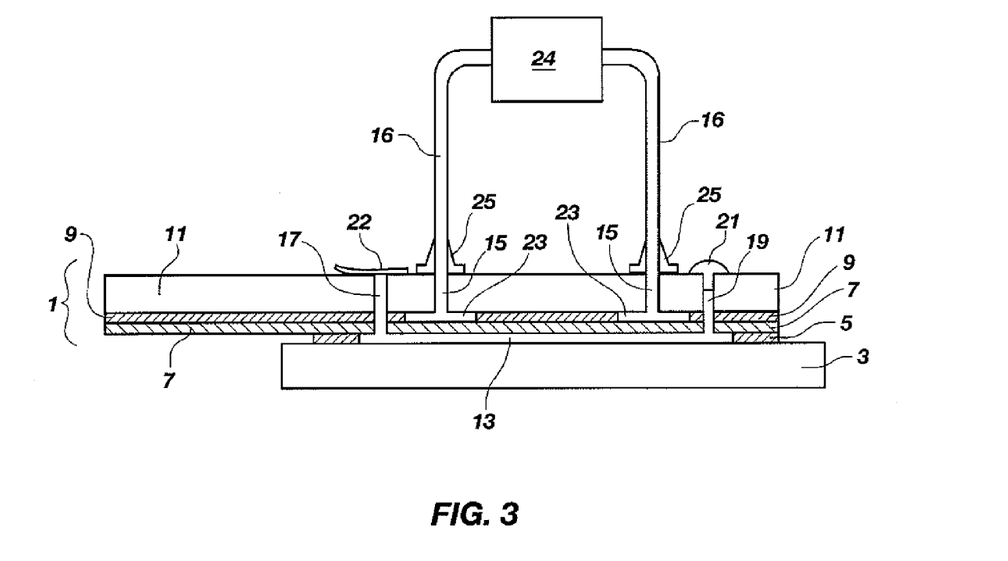
FIG. 3 is a cross-sectional view of the assembled device adhered to a microarray slide.

FIG. 2 breaks down device 1 into its components. In the embodiment of device 1 depicted in FIG. 2, the main structure of device 1 is a three-layer laminated structure, formed from main support layer 11, mixing bladder layer 9, and diaphragm layer 7. Main support layer 11 provides structure for the device. Attached to main support layer 11 is the mixing bladder layer 9. Within mixing bladder layer 9 are openings 10 for the formation of mixing bladders. Mixing bladder openings 10 are aligned with ports 15 in the main support layer 11. Diaphragm layer 7 is attached to the mixing bladder layer 9. The diaphragm layer 7 forms the floor of the mixing bladders, while the mixing bladder layer 9 forms the walls and the main support layer 11 forms the ceiling of the mixing bladders. Device 1 may be attached to a substrate such as glass microarray slide 3 by adhesive gasket 5 thereby forming a reaction chamber 13 that contains microarrayed spots, as illustrated in FIG. 3. Main support layer 11 includes inlet 17 and outlet 19, which allow materials to be loaded into or removed from the reaction chamber with the use of devices such as micropipettes or syringes. There are also openings for inlet 17 and outlet 19 in mixing bladder layer 9 in alignment with inlet 17 and outlet 19 openings in main support layer 11. Diaphragm layer 7 also has openings for inlet 17 and outlet 19 in alignment with inlet 17 and outlet 19 openings in main support layer 11 and inlet 17 and outlet 19 openings in mixing bladder layer 9. When the components of the device are assembled, inlet 17 and outlet 19 permit fluids to enter and exit the reaction chamber. Notches 6 and 8 in adhesive gasket 5, visible in FIG. 2, align with inlet 17 and outlet 19, so that the inlet 17 and outlet 19 are supported by the adjacent gasket material so that the reaction chamber does not collapse under the pressure of pipetting devices used for filling and emptying of the chamber. The inlet and outlet are compatible with devices suitable for introducing or extracting liquids, such as a micropipette or syringe. Removal tab 27 projects over the edge of microarray slide 3 allowing a user of the device to easily remove device 1 from microarray slide 3. Although reactions carried out in the reaction chamber formed by device 1 will normally be performed with liquid solutions, both inlet 17 and outlet 19 are preferably adapted to accommodate the flow of both liquids and gases. Upon initial filling of the reaction chamber, air present in the reaction chamber will escape out of outlet 19 as liquid is loaded via inlet 17. If a second solution is loaded into the reaction chamber, the first liquid will be forced out of outlet 19. Moreover, in some cases it may be desirable to inject air into reaction chamber 13 via inlet 17 to push out liquid already present therein. Therefore, the term fluid, as used herein, is intended to refer to both liquids and gases or gaseous mixtures.

FIG. 3 is a cross sectional view of device 1 attached to slide 3. The layer closest to the substrate, in this case a glass microarray slide 3, is adhesive gasket 5. Adhesive gasket 5 is also attached to diaphragm layer 7. Both inlet 17 and outlet 19 penetrate through the main support layer 11, mixing bladder layer 9, and diaphragm layer 7 of the device and are in fluid communication with reaction chamber 13. Ports 15 penetrate through main support layer 11 and connect to mixing bladders 23. Ports 15 are utilized to introduce pressure differentials to mixing bladder 23 and are compatible with connectors 25, which in this embodiment may be secured over ports 15 with adhesive, and which provide for connection to pneumatic tubing 16 capable of transferring pressure differentials from pressure source 24, which may be a pump, compressor, or other such device. A number of fittings may be used for connecting pneumatic tubing to the ports in the various embodiments of the microarray interface device, as are known or may be devised by those of ordinary skill in the art.

Figure 4:
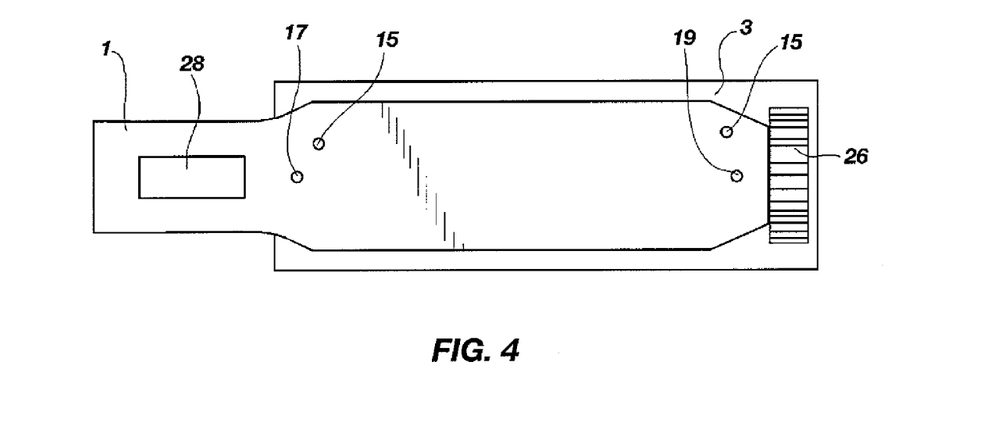
FIG. 4 is a top view of the device attached to a microarray slide.

As shown in the exploded view of FIG. 2 and the cross-sectional view of FIG. 3, adhesive gasket 5 defines the length, width, and height of reaction chamber 13. The internal dimensions of the gasket are preferably large enough to accommodate all of the arrayed spots. The ends of the opening in the gasket taper toward the fill and outlets to prevent the entrapment of air during loading. As shown in FIG. 4, the external dimensions of the device should be small enough to allow slide 3 to protrude past the edge of device 1 on one end of the slide to aid in disassembly and to allow room for appropriate identification such as bar code 26. A label 28 bearing a bar code or other identifying mark or information may also be placed on device 1. The gasket is preferably wide enough to allow for a reliable seal but narrow enough to not adhere to the slide so strongly that there is significant risk of slide breakage during disassembly. It is desirable to make the thickness of the adhesive gasket as small as possible to reduce the volume of the reaction chamber 13. For example, a 0.025 mm thick adhesive gasket that encloses a 20.5 mm×55 mm array area as used in one presently preferred embodiment of the invention produces a reaction chamber with a volume of about 38 μl.

Multiple versions of the microarray interface device can be produced with minor modifications in the laminated structure. Different versions will allow the units to interface with slides having a variety of array configurations while still being fully compatible with other components of a reaction system, which may include a hot block interface device, pneumatic tubing, clamp, and assembly jig. These modifications involve varying the length and width of the opening(s) in adhesive gasket 5 and relocating the positions of the mixing bladders 23, port 15, inlet 17, and outlet 19.

As illustrated in FIG. 2 and FIG. 3 the device may contain one or more air driven mixing bladders that may be reciprocally inflated and collapsed, to cause agitation and mixing of the solution within reaction chamber 13 on microarray slide 3. Diaphragm layer 7 forms the ceiling of reaction chamber 13. The portions of diaphragm layer 7 underlying mixing bladders 23 are displaced into or out of processing chamber 13 when mixing bladders 23 are inflated or deflated respectively. Pressure source 24 can be used to generate pressure differentials. Various types of pumps may be used as pressure source 24, and may be used in combination with various configurations of valves, manifolds, etc. to provide positive or negative pressure signals to mixing bladders in one or more devices in a desired pattern.

In the embodiments of the invention depicted in FIGS. 2–4, ports 15 exit device 1 via the top surface, with the openings located over reaction chamber 13. As described in connection with FIG. 3, pneumatic tubing 16 from pressure source 24 connects to connectors 25 attached to the surface of device 1 over ports 15. Because the port connections are located over reaction chamber 13, care must be taken not to apply excessive pressure to the device, which could in turn damage the microarray on the surface of slide 3. In order to eliminate this concern, and to make it possible to form port connections by clamping rather than an adhesive, in an alternative embodiment of the invention, port openings located in removal tab 27, with channels passing through the tab between the port openings and the mixing bladders.

Figure 5:
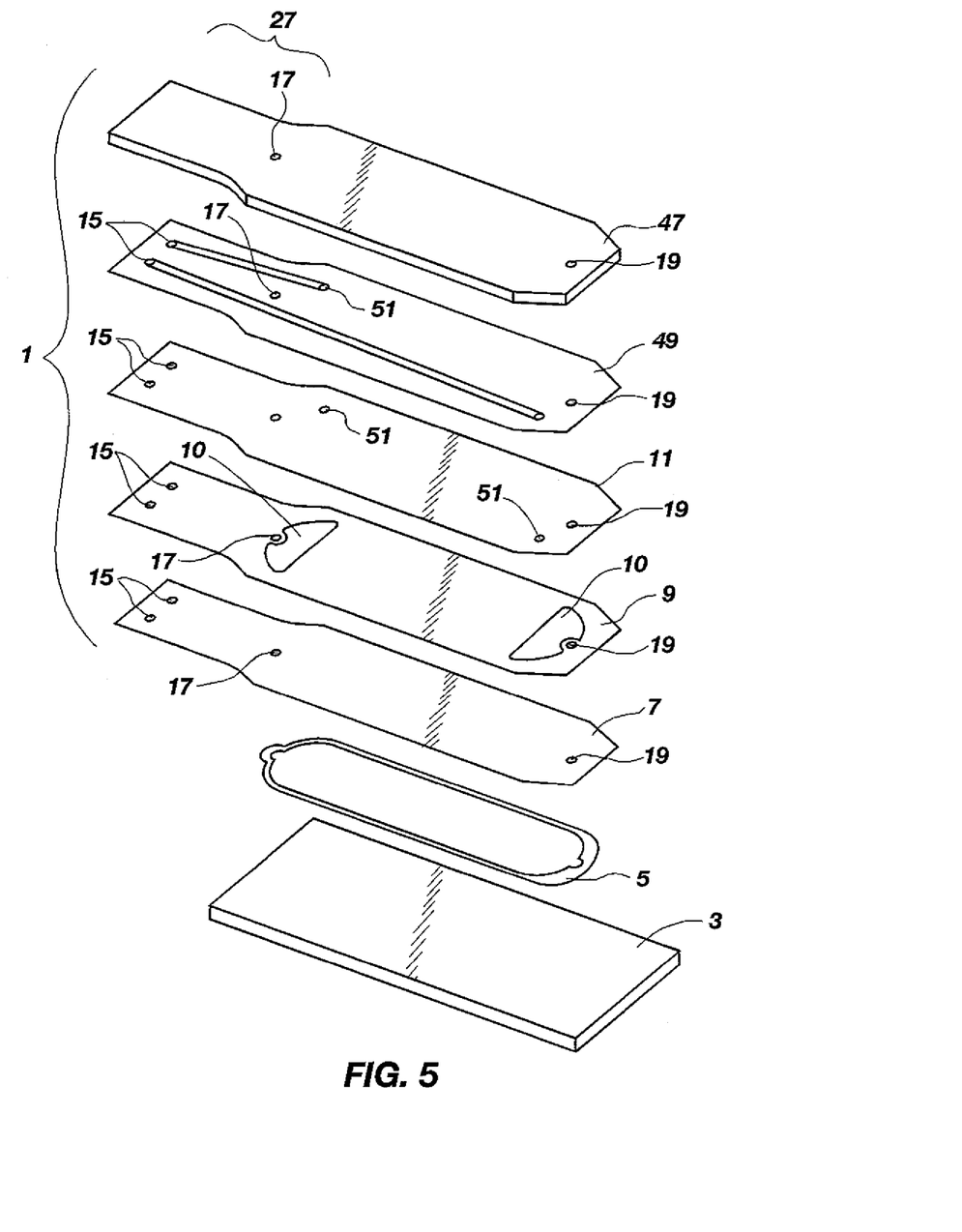
FIG. 5 is an exploded view of an alternative embodiment of the device that includes a top layer and an adhesive channel layer.

FIG. 5 depicts an exemplary embodiment of the device in which ports 15 are located in removal tab 27 rather than the top surface of device 1, with channels 51 providing communication between ports 15 and mixing bladders formed by openings 10 in mixing bladder layer 9. In this embodiment, in addition to the layers mentioned previously, adhesive channel layer 49 and top layer 47 are added. The device thus includes top layer 47, adhesive channel layer 49, main support layer 11, mixing bladder layer 9, diaphragm layer 7, and adhesive gasket 5. As described previously, adhesive gasket 5 functions to adhere the microarray interface device to a substrate such as glass microarray slide 3. In this embodiment, ports 15 in protruding removal tab 27 may interface with pressure lines from a pressure source. Removal tab 27 may be clamped against O-rings or other sealing devices to carry pressure differentials through channels 51 in adhesive channel layer 49. Channels 51 penetrate through main support layer 11 and terminate in openings 10 in mixing bladder layer 9. Length, width and depth of channels 51 are defined by channel layer 49. The channels are bounded by top layer 47 and main support layer 11. The mixing bladders are contained within main support layer 11 and diaphragm layer 7, with mixing bladder layer 9 forming the width, length, and depth of the mixing bladder. Inlet 17 and outlet 19 extend through all layers except adhesive gasket 5 and terminate in the reaction chamber. Channels 51 extend through diaphragm layer 7, mixing bladder layer 9, main support layer 11, and channel layer 49, and terminate in ports 15, which open on the underside of removal tab 27 in the embodiment of FIG. 5.

Figure 6:
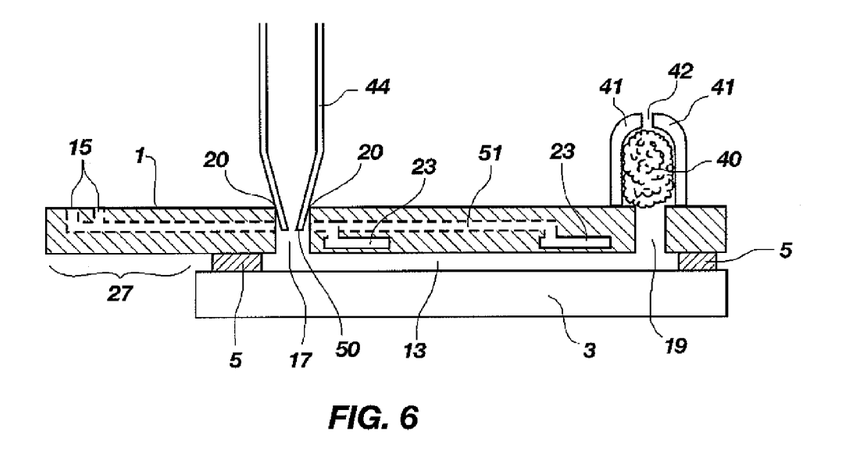
FIG. 6 illustrates the use of a pipette for filling and waste collection cap for retrieval of waste liquids.
Figure 12:
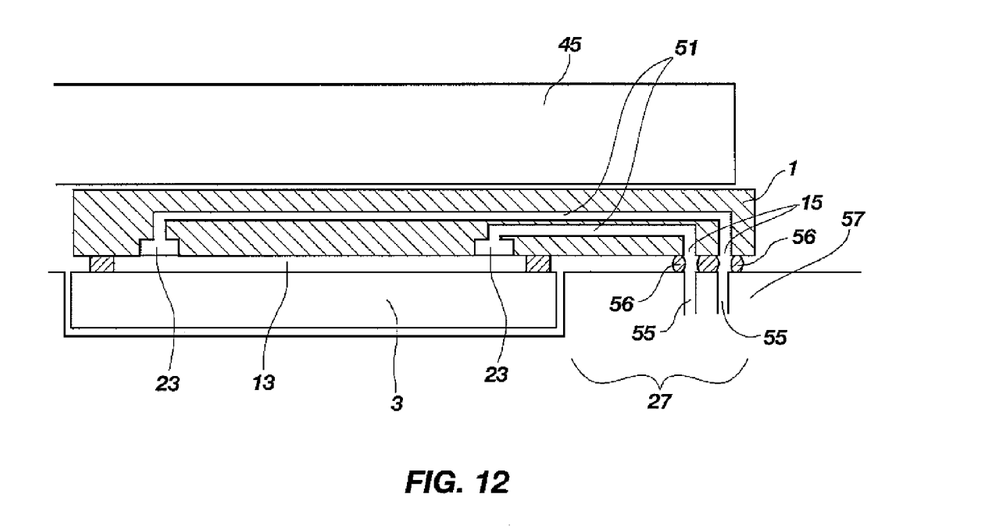
FIG. 12 illustrates a clamp positioned over the assembled device attached to a microarray slide.

In the embodiment of FIG. 5, a five layer main structure is depicted, with mixing bladder openings 10 and channels 51 formed in separate layers. However, various alternative configurations using larger and smaller numbers of layers may be used to form the main structure of device 1 with channels extending through removal tab 27. For example, channels 51 may be formed in mixing bladder layer 9, continuous with openings 10. Alternatively, channels may be formed in different layers of the structure. Various equivalent designs for forming mixing bladders, channels, ports, and fill and outlets within device 1 may be devised by those of ordinary skill in the art and are considered to fall within the scope of the invention. Moreover, openings 15 connecting to channels 51 may be located on either the lower side of removal tab 27, as depicted in FIGS. 5 and 12, or the upper side of removal tab 27, as depicted in FIG. 6. Though less preferred, it would also be possible for openings 15 to exit device 1 on an edge rather than a top or bottom surface.

In use, device 1 is first adhered to slide 3 to form a reaction chamber 13 on slide 3, as depicted in FIG. 6. Solution is then loaded into reaction chamber 13 through sample inlet 17 with, for example, a syringe or micropipette 44. It is important that syringe or micropipette 44 forms a sealing fit with edge 20 of inlet 17. It is also important that when syringe or micropipette 44 is sealed against edge 20 of inlet 17, tip 50 does not touch the surface of slide 3, as this may damage the surface of the slide and compress tip 50, thereby impeding the flow of fluid. As fluid enters reaction chamber 13, air may escape via outlet 19. Alternatively, if reaction chamber 13 is compressed or evacuated prior to filling, it may not be necessary to provide an outlet through which air may escape. However, normally on the initial filling of the device, outlet 19 will be left open. On subsequent fills, liquid displaced from reaction chamber 13 may be collected in waste collection cap 41, shown in position over outlet 19 in FIG. 6, and described in detail subsequently. Inlet 17 and outlet 19 are preferably small to minimize the dead volume contained within, and may be supported from below by adhesive gasket 5 adjacent to notches 6 and 8, as discussed previously, such that they do not collapse against the surface of slide 3 when pressure is applied by a pipette or, more preferably, a micro syringe fitted with a standard pipette tip used to introduce solution into reaction chamber 13. It has been found that a positive displacement pipettor that has minimal or no dead air space above the liquid sample, e.g. an Eppendorf Combitip™ pipettor, is especially suited for generating pressures sufficient to load fluid into the reaction chamber. Following addition of a solution, each of inlet 17 and outlet 19 may be sealed with a plug 21 as illustrated on outlet 19 in FIG. 3, or with a piece of adhesive tape 22, as illustrated on inlet 17 in FIG. 3. If pieces of adhesive tape are used, they are preferably manufactured with non-adhesive tabs for easy manipulation. Plugs 21, as illustrated in FIG. 6, may be machined, molded, etc. from plastic, metal, or other suitable materials.

Figure 7:
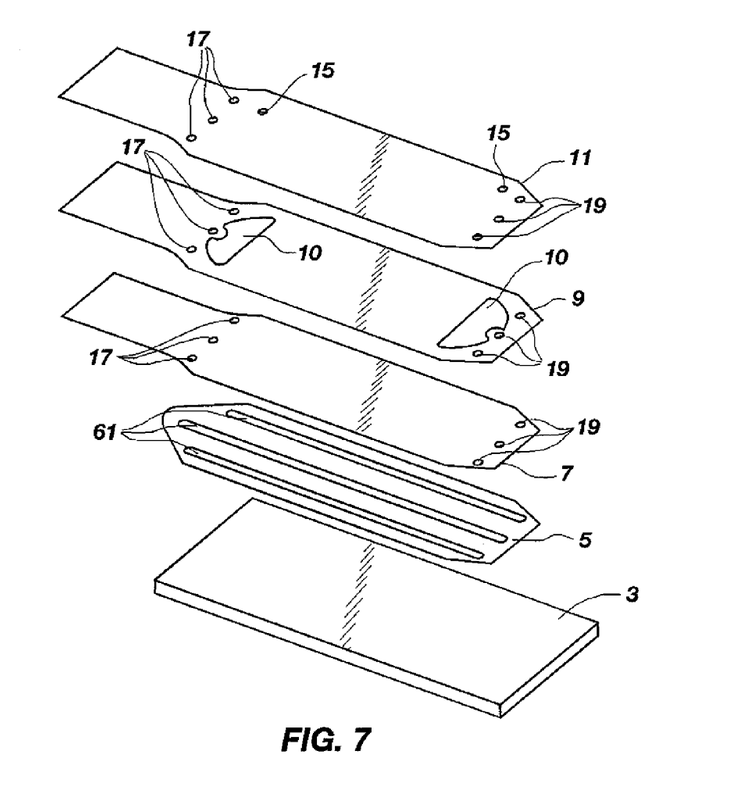
FIG. 7 is an exploded view of an alternative embodiment with multiple reaction chambers.

A preferred embodiment of the invention has two pneumatically driven mixing bladders. The device may also be made with just one mixing bladder, or with more than two mixing bladders. It is also within the scope of the present invention to produce mixing in multiple reaction chambers with the use of just one or two mixing bladders, by having each mixing bladder overlie portions of all or some of the reaction chambers. In particular, as shown in FIG. 7, multiple parallel elongated reaction chambers may be formed with the use of gasket 5 having multiple parallel slots 61, and the mixing bladders defined by openings 10 in mixing bladder layer 11 may be positioned to overlap the ends of the reaction chambers. Other arrangements of multiple reaction chambers are also possible. Multiple openings having any other suitable configuration, rather than multiple parallel slots 61 as depicted in FIG. 7, may be used to form multiple reaction chambers on the substrate. It is also possible to have multiple inlets 17 and outlets 19 to access these multiple reaction chambers. Ports 15 function as described previously.

Figure 8:
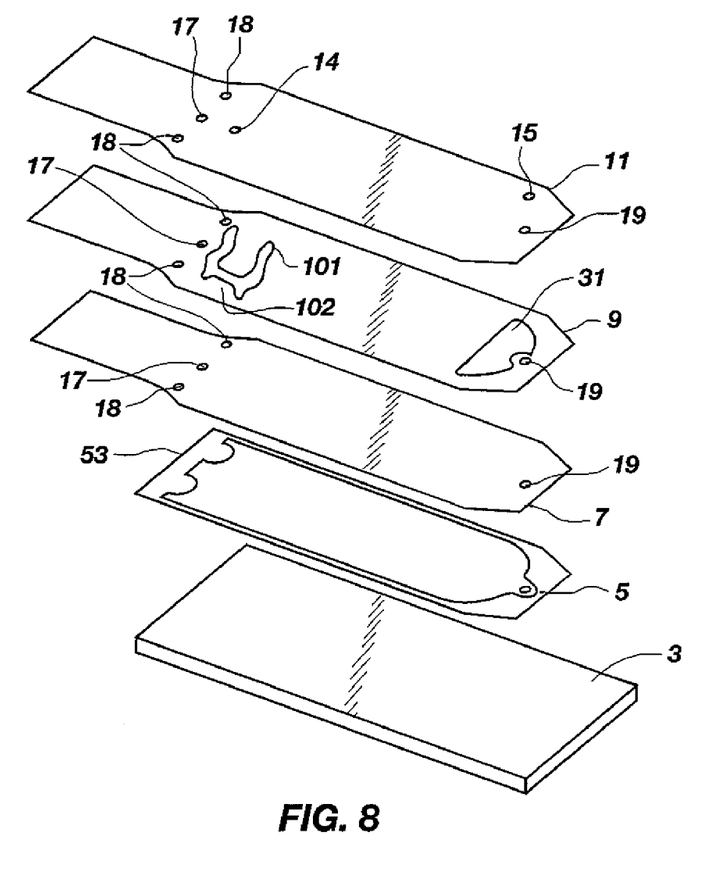
FIG. 8 is an exploded view of an alternative embodiment of the device that utilizes deflection chambers.

The interface device can be modified to interface with slides 3 that are spotted less than 8 mm from one edge of the slide. The gasket of the standard device would cover some spots of such slides. To avoid this, adhesive gasket 5 may be squared off on one end 53, as in the alternative embodiment shown in FIG. 8. However, there is no area at this end of the reaction chamber where a diaphragm can be placed such that it would not contact array spots when inflated. To avoid potential damage to these array spots, mixing bladder layer 9 is modified to contain two or more narrow openings 100 and 101, neither of which is driven by reciprocating air pressure. Openings 100 and 101 are formed at squared end 53 of the adhesive gasket 5, and when component layers of FIG. 8 are pressed together, form deflection chambers with dimensions defined by mixing bladder layer 9 and contained between main support layer 11 and diaphragm layer 7. Rather than being attached directly to a pressure source, this passive deflection mixing bladder responds to the fluid pressure created by an actively inflated and/or deflated force mixing bladder by deflecting passively inward or outward. The force mixing bladder is formed by opening 31 in the mixing bladder layer. The force mixing bladder may have dimensions identical to the mixing bladder discussed previously. Openings 100 and 101 may be connected by one or more channels 102 in the mixing bladder layer 9. At least one vent 14 in main support layer 11 connects at least one opening, in this example opening 101, to the atmosphere. Ports 15, inlets 17, and outlets 19 function in the invention as described previously. Air escape ports 18 extend through main support layer 11, mixing bladder layer 9, and diaphragm layer 7 and are in communication with the reaction chamber and allow gas to escape from the reaction chamber. Air escape ports 18 are compatible with caps, port adapters, and other devices used with inlets 17, outlets 19, and ports 15.

Mixing

As discussed previously, to drive mixing within the reaction chamber, air moves into and out of mixing bladders 23 via ports 15 and channels 51. Ports 15 may exit device 1 on its top surface, on the top or bottom surface of removal tab 27, or even on an edge. Port connectors 25 may attach over ports 15 via double-sided adhesive tabs, as depicted in FIG. 3, and connectors 25 in turn may be connected to various pressure sources 24, such as a reciprocating air pump or other pressure or vacuum sources.

Figure 14:
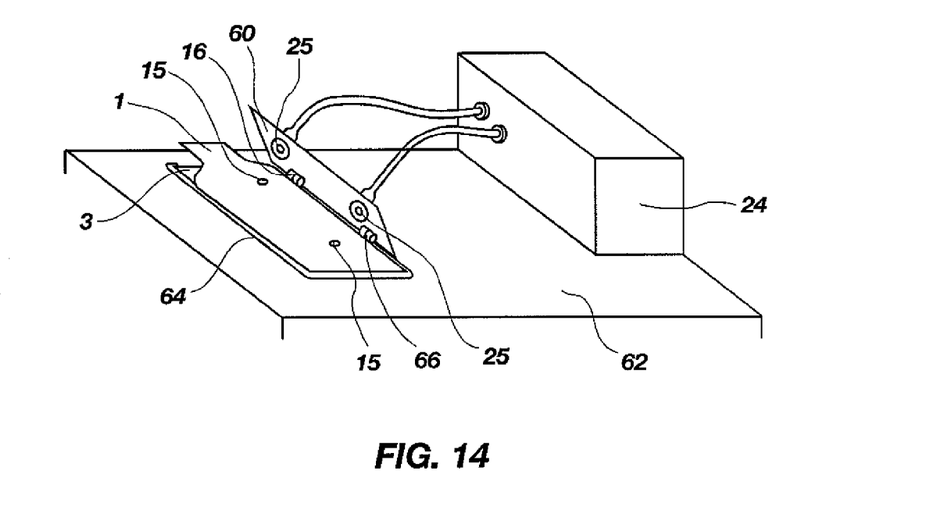
FIG. 14 depicts a method of positioning and supporting port connectors with respect to the device.

As illustrated in FIG. 14, alignment of connectors 25, which communicate with pressure source 24, with ports 15 may be simplified by mounting connectors 25 in an alignment means 60 that is adapted to bring connectors in proper alignment with ports 15. Alignment means 60 may be movably mounted with respect to a base 62 on which slide 3 (with attached interface device 1) is positioned. Slide 3 is positioned with respect to base 62 by fitting it into recess 64, for example, or by other means as known by those of ordinary skill in the art. Alignment means 60 may be mounted with respect to base 62 (and hence with respect to interface device 1) in such a manner that it can be moved out of the way to permit positioning of slide 3 on base 62, and then moved back into position over slide 3 such that connectors 25 are positioned correctly with regard to ports 15. In the example shown in FIG. 14, alignment means 60 is rotatably mounted with respect to base 62 by means of hinges 66. Alignment means 60 is depicted in an open configuration in FIG. 14; it would be rotated downward to bring port connectors 25 into contact with ports 15. Alignment means 60 may be movably mounted with regard to base 62 in such a way that it slides or translates, rather than rotates, into position. It would also be possible for alignment means 60 to not be connected to base 62, but to be aligned with base 62 with the use of alignment pins or the like. If connectors 25 are secured over ports 15 with an adhesive, it is not necessary for alignment means 60 to apply any pressure to hold them in place with respect to device 1. In fact, if connectors 25 attach to the top surface of device 1, it is preferred that it not apply pressure, as this may deform the reaction chamber and possibly damage the reactants on the surface of slide 3. An advantage of using this mechanism for connecting the pressure source to ports 15 is that a simpler microarray interface device, as depicted in FIGS. 2 and 3, can be used, rather than one with a larger number of layers and ports 15 in removal tab 27, as depicted in FIG. 5.

Alternatively, a clamping connection may be made between a pressure source and ports in removal tab 27, as depicted in FIG. 12. In a preferred embodiment, the ports are flush with the top layer of the device, but in alternative embodiments may protrude above the surface of the device. In another alternative embodiment liquid may be used to carry pressure differentials rather than a gas such as air.

Mixing is achieved within the reaction chamber by alternating between generating positive and negative pressures at each port thereby increasing or decreasing the pressure in each mixing bladder. According to Pascal's Principle, this pressure difference is distributed equally within the mixing bladder, resulting in bending of the diaphragm layer as discussed below. Separate pumps could also be used to generate pressure differentials. Pumps other than an air pump, including syringe pumps and compressors, could also be used.

The flexible diaphragm layer responds to changes in pressure within the mixing bladder. The main support layer responds less to a pressure change. As the pressure within the mixing bladder increases, the tendency of the diaphragm layer to bend into the reaction chamber increases. Intrusion of the diaphragm layer into the reaction chamber displaces solution within the reaction chamber. Displacement of the solution results in movement of the solution over any chemical spots on the surface of a microarray substrate. Likewise, decreased pressure in the mixing bladder sucks the diaphragm layer into the mixing bladder creating a vacuum for solution within the reaction chamber to occupy, resulting in movement of the solution over any chemical spots on the surface of a microarray substrate. By inflating and deflating the mixing bladders 180° out of phase, fluid may be moved back and forth over the surface of the slide.

It should be noted that pressure may be transmitted to the mixing bladders by another gas or gaseous mixture, or by a liquid such as water, oil, etc., rather than air, with corresponding appropriate selection of a pressure source and possible minor modification to the interface device. References are made throughout this document to mixing bladders, ports, pressure lines, etc., operating in connection with air pressures, but it should be understood that the invention is not limited to air as the medium by which pressure is transmitted to the mixing bladders to generate mixing, and that other fluids (gas or liquid) are considered to fall within the scope of the invention as materials suitable for transmitting pressures to the mixing bladders or mixing bladders. Pressure sources may pressurize gas or liquids to either positive or negative pressures in order to drive mixing in the inventive device.

Assembly and Manufacturing

Various materials may be used to prepare the microarray interface device within the scope of the present invention. Suitable materials for use in the device may be selected to meet desired functional requirements including appropriate flexibility, rigidity, durability for the supporting layer and diaphragm layer, appropriate adhesion properties for the adhesive gasket material, acceptable level of outgassing for all materials, and desired surface properties of hydrophilicity or hydrophobicity.

In the presently preferred embodiment of the invention, the main structure of the laminated interface device is constructed from alternating layers of adhesive and non-adhesive sheet materials, such that non-adhesive layers are adhered together by adhesive layers. Adhesive layers are preferably formed by adhesive sheet materials. Both adhesive and non-adhesive sheet materials may have openings cut through them to define mixing bladders, channels, fill or outlets, and other such structures. As an alternative to using adhesive sheet materials, it would also be possible to use adhesive materials that came in liquid form and were applied directly to non-adhesive layers. It would be possible to apply liquid adhesive materials in a pattern, by printing or silk screening techniques, in order to form channels, bladders, or other structures between non-adhesive layers. Layers may also be bonded together with thermal or solvent means.

Each layer of the device has properties unique to that layer. The materials preferred in the manufacturing of the device establish those properties. The manufacturing method employed may also be a factor in choosing construction materials. Layers in the device whose main purpose is to provide structure, such as main support layer 11 in FIG. 2 or top layer 47 in FIG. 5, are preferably constructed from a copolyester plastic such as EASTAR 6763 (Eastman Chemical Co., Kingsport, Tenn.). The diaphragm layer, which must deflect to produce mixing, is preferably constructed from a polyester film. 3M Scotchpar™ P581291, a polyester film having a prime coating on one surface, is used in the presently preferred embodiment of the invention. The prime coating surface is oriented to form the inner surface of the reaction chamber, and also is the surface to which the adhesive gasket adheres. The gasket binds more strongly to the prime coated surface than to the slide, making it possible to remove the hybridization chamber forming device cleanly from the slide. These materials are preferred for use in devices used for performing hybridizations at about 42° C., and it will be appreciated that for reactions performed under other conditions, other materials may be more desirable. Accordingly, other plastics may be used in construction of the device, with physical and chemical properties selected for the particular reaction conditions. The reaction chamber is preferably of uniform height, which is accomplished by constructing the adhesive gasket, in addition to any other layer, using semi-rigid, stock, sheet and film materials, which tend to be of uniform thickness. All materials must be compatible with any chemicals or reactants that they contact, and not be deteriorated by such contact, nor interfere with the chemical reactions performed within the device.

The mixing bladder layer, adhesive channel layer, and adhesive gasket are preferably formed of adhesive materials. The adhesive gasket is preferably formed on the bottom of the device, on the diaphragm layer. Importantly, the gasket should be capable of creating a gas tight seal around the reaction chamber while being able to be compressed to create the desired chamber volume. It is important that when the device is removed from the slide, the gasket remain bound to the device and not the slide, since gasket material remaining on the slide would interfere with the slide reader. The adhesive must thus bind preferentially to the diaphragm layer rather than the slide. A variety of removable and repositionable adhesives may be used. Acrylic transfer film (e.g., 501 FL, 3M, St. Paul, Minn.) has been found to function in a satisfactory manner in devices used for hybridization. It is available in 25 µm thickness, thus providing a 25 µm chamber height. Other adhesives that may be used include, but are not limited to, acrylic, urethane, silicone, and rubber adhesives. Such materials are resilient and subject to plastic and/or elastic deformation. The adhesive gasket may be formed from a commercially available adhesive film, which may also be used to form mixing bladder layer and adhesive channel layer, as described above. Gasket materials may alternatively be applied to supporting layers by spray coating, silk screening, pad printing or other printing method that produces a suitable finish and thickness. The adhesive gasket may be constructed in such a way that a release liner covers the adhesive portion of the adhesive gasket. If the device is used in combination with a clamp to secure it to a substrate the seal or gasket could be made of any plastically deformable material, such as Parafilm™, or an elastomeric material such as silicone rubber, polyurethane, polybutadiene methacrylate rubber, or any other suitable material that can be compressed to create a seal.

The assembly process is preferably performed in a particle free environment to avoid trapping particles between laminate layers, which can negatively impact both reaction chamber uniformity and reliable sealing. If the polymeric sheet materials of the preferred embodiment of the device are used, it is preferred that the materials are degassed by exposure to a vacuum for a period of time sufficient to prevent the materials from releasing significant amounts of gases during use of the device, which may cause the formation of bubbles within the hybridization chamber. Degassing will be accomplished most rapidly if the parts are degassed prior to assembly; however, it is also possible to degas the device subsequent to assembly. The particular degassing requirements will depend on the specific materials used and the specific device configuration, and the optimal parameters must be determined on a case by case basis. For a device constructed from the presently preferred polymeric sheet materials, we have found that degassing the parts for 2–3 hours at about 0.05 Atm pressure and a temperature of 45° C. provides satisfactory results. Following assembly, the device may be cleaned and packaged to ensure it stays clean. A clean device will form a reaction chamber that will fill reliably and produce better reaction results. Because positive pressure is needed to rapidly inject probe, the inlets are preferably manufactured in a uniform manner such that they seal tightly with the pipette tip or other device used to inject sample. Manufacturing of the inlets must not produce a lip that projects into the reaction chamber and interferes with filling and sealing.

The manufacturing and assembly of the microarray interface device is important to ensure: 1) thickness and uniformity of the reaction chamber, 2) a highly reliable seal, 3) vapor bubbles or particles are not introduced into the reaction chamber, 4) reliable filling, and 5) proper interfacing with other adhesive laminate microarray interface device components. Therefore, the materials that comprise the laminate device are preferably cut without introducing deformations or burrs, and assembled with sufficient alignment tolerances. For example, the various layers of the device. may be cut using automated processes, such as die-cut processing. Other methods include but are not limited to layer cut processing and injection molding.

Relationship to Other Elements

The microarray interface device can be used in conjunction with other elements. A microarray slide with attached microarray interface device may be placed on a commercial or custom built hot block or slide warmer. The hot block or slide warmer may hold multiple microarray slides with an attached device. The hot block or slide warmer serves to bring to and maintain at a desired temperature the slide, interface device, and any components reacting within the reaction chamber. In a custom built hot block device for use with the pneumatically actuated microarray interface device a pressure source, manifold and pressure line connection may be incorporated into the hot block device. As mentioned previously, an air pump may be connected to the device via pneumatic tubing. The tubing preferably connects to the ports, said ports terminating in the mixing bladder. Alternatively, openings for the transmittance of pressure differentials in the base unit may interface with ports in the removal tab of the device. An pressure manifold attached to a pump may be used for controlled distribution of pressure differentials to multiple devices simultaneously. Pneumatic tubing extending from the pressure manifold and attaching to the ports on the microarray interface device transmit the pressure differentials into the mixing bladders contained within the device.

Figure 9:
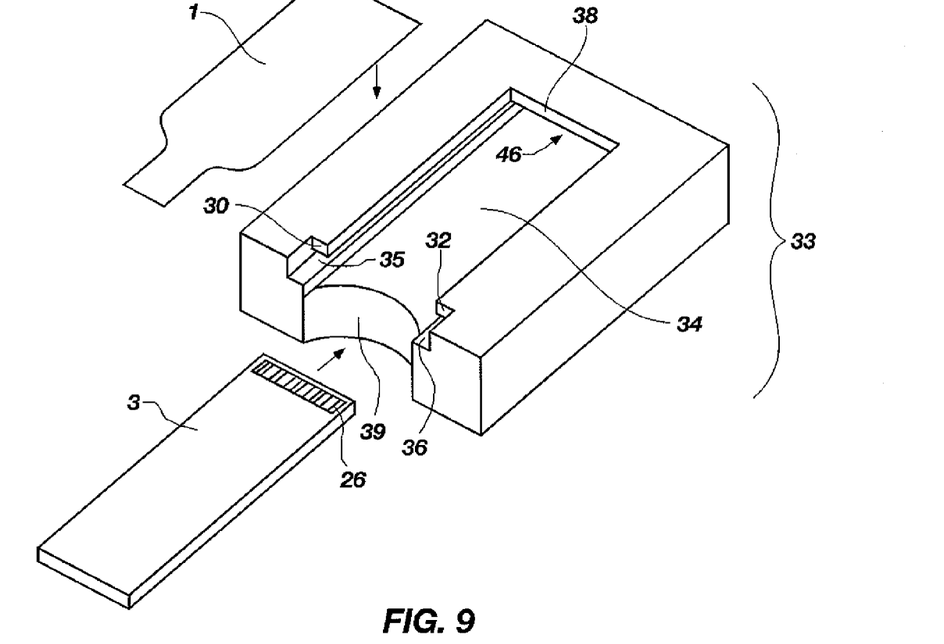
FIG. 9 shows an alignment jig for positioning the device with respect to the slide.

To assist with assembling microarray interface device 1 to glass microarray slide 3, and removing device 1 from the slide following hybridizations, a simple reusable alignment jig 33 as depicted in FIG. 9 may be used to ensure proper positioning of slide 3 and device 1. The edges of slide 3 are inserted into a slot comprising grooves 35 and 36 in jig 33. Grooves 35 and 36 are raised above surface 34 of alignment jig 33 preventing friction between surface 38 and slide 3 when slide 3 is inserted into alignment jig 33. Notches 30 and 32 above grooves 35 and 36 allow a user of jig 33 to drop one end of slide 3 directly into grooves 35 and 36, to facilitate insertion of slide 3 into grooves 35 and 36. To assist with proper alignment of the device 1 over the slide 3, grooves 35 and 36 extend past overhang 38 into recess 46. When slide 3 is fully inserted into grooves 35 and 36, the end portion of the slide 3 bearing bar code 26 resides in recess 46, and overhang 38 is situated at a distance from the end of slide 3 that is the preferred position for the end of device 1. Once slide 3 is positioned in jig 33, the release liner is removed from device 1 to expose the adhesive gasket. The end of device 1 opposite the removal tab is aligned flush against overhang 38, thus positioning device 1 in a preferred position over an inserted slide 3. The device 1 is then placed directly or gently rolled onto the microarray slide, so that it adheres to slide 3 via adhesive gasket 5. Jig 33 is preferably constructed from a rigid material such as plastic or metal, which will be unharmed by exposure to salts and moisture as well as possess the necessary mechanical properties.

Figure 10:
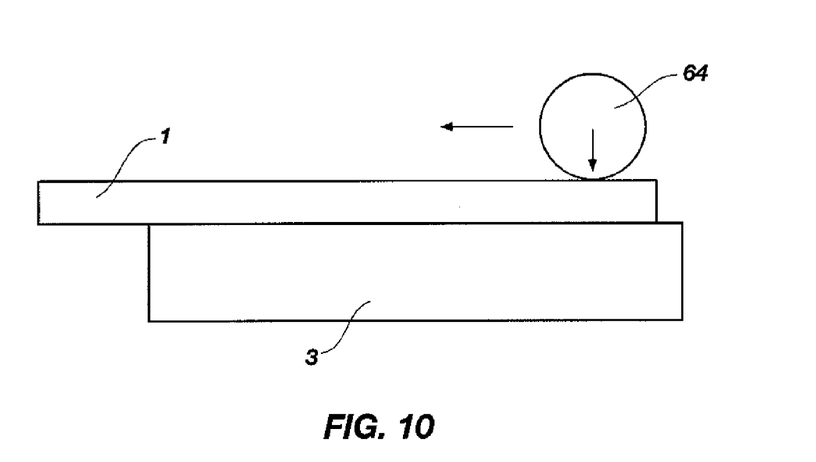
FIG. 10 illustrates the use of a rolling apparatus used to seal the device to a microarray slide.

A brayer having a straight, rigid edge, such as an acrylic block, is run over the top of the device to ensure that the adhesive gasket is adhered securely to slide 3. Alternatively, a roller 64 may be used as depicted in FIG. 10. While being pressed firmly against device 1, roller 64 is moved across the length of microarray slide 1. This supplies sufficient pressure to the adhesive gasket to ensure a proper seal and to prevent air bubbles from being trapped between the adhesive and the slide. In an alternative embodiment, the alignment jig may include a brayer apparatus that moves horizontally across the jig pressing and sealing the device to the slide. Another method of sealing interface device 1 to the slide is to use a press that applies uniform direct pressure to the interface device 1 to press it against glass slide 3 or another substrate.

Following completion of the desired reaction and possibly removal of any fluids from the reaction chamber, the slide with interface device attached is replaced in the alignment jig. It may be desirable to maintain the slide at an elevated temperature (e.g. about 42° C.) to facilitate complete removal of the adhesive gasket from the slide surface. Referring back to FIG. 9, indentation 39 in jig 33 allows the user to grasp removal tab 27 portion of the device 1 and peel the device 1 away from the slide 3. The flexible nature of the adhesive laminate device 1 makes it possible to bend device 1 to aid in removal of device 1 from the slide. Although jig 33 depicted in FIG. 9 may be used in both assembly and disassembly of the interface device and slide, it would also be possible to construct separate jigs for assembly and disassembly, since disassembly does not require all of the same features of the jig as does assembly.

Figure 11:
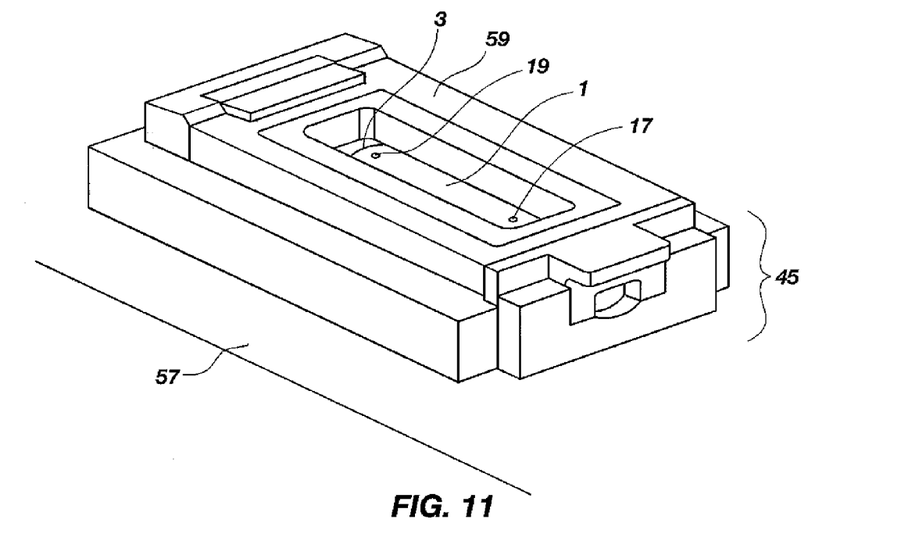
FIG. 11 depicts a clamp for clamping the device on an instrument.

Clamp 45, shown in FIG. 11, may be used to secure device 1 to a substrate such as microarray slide 3. Clamp 45 may be mounted to instrument base unit 57, which may include a temperature control unit, pressure source, and so forth. Clamp 45 may assist in sealing device 1 to a microarray slide 3 as well as securing microarray slide 3 to base unit 57. Device 1 ensures good thermal contact between microarray slide 3 and base unit 57. Opening 59 in clamp 45 allows a user of the device to access inlets 17 and outlets 19 on the surface of device 1. One opening 59 is shown but multiple openings could also be used. When clamp 45 is secured over device 1 attached to a microarray slide 3, these openings allow for introduction or extraction of fluids from the reaction chamber without removal of the clamp. Additional gaskets or O-rings may connect internal channels in clamp 45 to ports in the device 1.

In a preferred embodiment shown in FIG. 12, clamp 45 aids in sealing removal tab 27 of device 1 to base unit channels 55 in base unit 57. O-rings 56 may be used to ensure a tight seal between base unit channels 55 and channels 51 in device 1. Base unit channels connect to a pressure source contained in base unit 57, which supplies positive and negative pressures to mixing bladders 23 via channels 51 to generate mixing in reaction chamber 13, as discussed previously.

As described previously, a syringe or micropipette will be used to introduce fluids into reaction chamber 13 through inlet 17. A shown in FIG. 13, a disk-like inlet adapter 43 may be placed over either inlet 17 or outlet 19. Port adapter 43 interfaces with the tip a micropipette, pipette, or syringe 44 stabilizing micropipette, pipette, or syringe 44 in an upright position. Port adapter 43 stabilizes pipette 44 in inlet 17, allowing a user of the device to use both hands to push a fluid from a micropipette or other such device into inlet 17. As the fluid is pushed into inlet 17 and reaction chamber 13, fluid previously occupying reaction chamber 13 is pushed out outlet 19 and into micropipette 44 or other such device held by port adapter 43. Such an adapter can be constructed by drilling a hole sized to receive the pipette tip in a piece of plastic, which can be adhered to the interface device with double sided tape, with the hole aligned over the desired port.

After reaction chamber 13 has been filled, an adhesive tab 22, plug 21, or other sealing structure, may be placed over each inlet 17 and outlet 19 to seal reaction chamber 13, as shown in FIG. 3. Plug 21 may be made from stainless steel, polycarbonate, or a variety of other materials. After the initial filling of reaction chamber 13, when additional fluid such as a wash solution or other reagent is introduced to reaction chamber 13, fluid already in reaction chamber 13 is pushed out of outlet 19. As illustrated in FIG. 6, waste collection cap 41 may be placed over outlet 19 to absorb fluid as it leaves outlet 19. Waste collection cap 41 may be made from various plastics or metals. Waste collection cap 41 is filled with absorbent material 40, such as a sponge or dry tissue, which wicks liquids through outlet 19. An air vent 42 in waste collection cap 41 allows air to escape as liquid enters. The liquid collected in the absorbent material 40 may be disposed of or retrieved for analysis or reuse.

Use of Microarray Interface Device

A preferred method of utilizing the present invention is in the performance of hybridization reactions on a microarray slide. When the present invention is used for hybridization, the reaction chamber can be referred to as a hybridization chamber. The microarray user starts with a prehybridized and dried slide prepared using standard protocols. A release liner is removed from the microarray interface device to expose the adhesive gasket. This gasket is attached to the slide with the alignment jig as discussed above and pressed against the slide to form a seal with the use of a brayer, roller or press as described above. The user sets the microarray slide with attached device in a slot in a hot block so it can come to temperature, and moves on to assembling additional slides. The hot block has multiple slots to process multiple slides simultaneously. The adhesive laminate structure of the microarray interface device minimizes the thermal mass of the device allowing it to come to temperature quickly. Using the exemplary device described herein, about 38 µl of prewarmed (e.g., to about 42° C.) probe solution is injected into the inlet using a micro syringe fitted with a pipette tip or a positive displacement pipet such as an Eppendorf Combitip™ pipettor, as described above. It is typically preferable to load a slightly larger volume of solution into the pipette to ensure complete filling. As solution enters the hybridization chamber via the inlet, air escapes via the outlet. The hybridization chamber fills more quickly and easily if the slide/lid is prewarmed (e.g., to about 42° C.), probably due to the lower viscosity of the carrier DNA in the probe solution at higher temperatures. The inlets are sealed with adhesive tabs, the port connectors are attached, the mixing bladders are alternatively inflated and deflated, and the hybridization is allowed to proceed. Appropriate temperature is maintained by the temperature controller.

Following hybridization, the inlet adhesive tabs may be removed. In some cases it may be desirable to collect the used hybridization solution and recover the probe from the solution. The used probe can be recovered as follows: prewarmed hybridization solution (minus DNA or other probe) is injected into inlet 17, and the hybridization probe plus additional hybridization solution (minus DNA or other probe, as noted above) is pushed out of outlet 19, where it may be collected by being pushed into or wicked into a pipette tip, piece of absorbent material, or other collection device, such as a waste collection cap 41 as shown in FIG. 6, placed at outlet 19.

Figure 13:
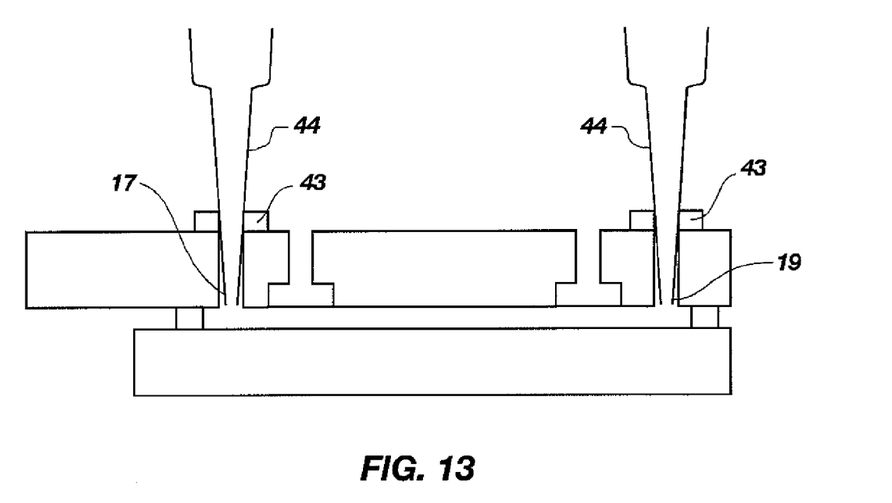
FIG. 13 depicts the placement of a port adapter.

If the collection device is a pipette tip, it may be affixed to the outlet using a port adapter as shown in FIG. 13. After the recovered probe has been received in the pipette tip, a piece of tape may be placed over the top of the pipette tip to form an air tight seal, and the pipette tip removed from the outlet and the recovered probe solution reused as desired. The recovered probe may be reconcentrated using micro filtration spin columns.

Following probe recovery the slide may be subjected to an additional washing step. Pre-warmed wash buffer, for example, one or two applications of 200 µl, may be injected into the inlet, and waste wash buffer that is pushed out of the outlet may be captured using a specially designed disposable waste collection cap, as described previously, or simply wicked into a piece of absorbent tissue or the like. After these washing steps have been completed, the device may be peeled away from the slide utilizing the alignment jig and the slide placed in pre-warmed wash buffer in a wash rack. Clean removal of the device from the slide is accomplished by using a diaphragm material that has a higher affinity for the gasket material than does the pre-hybridized slide. Once all slides are in the wash rack, the washing process begins. The first wash proceeds for sufficient time to minimize the time differences between disassembly of the first and last slide.

It is possible to skip the wash steps prior to disassembly and disassemble the device with the assembly/disassembly jig submerged in wash buffer to prevent dehydration of the assay materials prior to subsequent wash steps. It is desirable to avoid dehydration of the assay materials, as this may lead to increased background signal. The wash buffer may be maintained at an elevated temperature to facilitate complete removal of the gasket from the slide.

Although the foregoing discussion has focused on the use of the microfluidic interface mixing device in connection with conventional microarray slides, the present invention may also be used to process cytology or histology slides, or slides with any other types of material which are subject to processing by delivering fluids to the surface of the slide. The chamber on the slide surface may be referred to as a hybridization chamber when the device is used with microarray slides, or with other slides on which DNA hybridization is to take place. When used with other applications, the chamber may be described as a reaction chamber.

The present invention, which has been described in several exemplary preferred embodiments, can be modified in many different ways without departing from the scope of the invention, which is defined by the appended claims.

The invention claimed is:

1. A microfluidic interface device for adhering to a substrate to form a sealed reaction chamber, comprising:
    a flexible main structure comprising a plurality of substantially planar flexible layers laminated together, wherein the layers comprise:
    a support layer;
    a diaphragm layer laminated directly or indirectly to the support layer; and
    at least two mixing bladders disposed between the support layer and the diaphragm layer; and
    an adhesive gasket laminated directly or indirectly to the diaphragm layer of said main structure, wherein said gasket defines the wall of a reaction chamber and is adapted to reversibly seal against a substrate to form a closed reaction chamber, said reaction chamber bounded by said substrate, the diaphragm layer, and said gasket;
    wherein said flexible main structure is sufficiently flexible that the gasket is capable of being released from the substrate without breaking the substrate during disassembly; and
    wherein each mixing bladder has at least one port providing communication between said mixing bladder and the exterior of said main structure and is adapted to connect to an external source of pressure or vacuum to produce alternate inflation or deflation of said mixing bladders and out of phase deflection of the diaphragm overlaying each opening of the mixing bladder layer, to thereby cause mixing of the fluid in the chamber.

2. The device of claim 1, wherein said main structure further comprises a removal tab adapted to be grasped by a user to facilitate removal of said device from a substrate to which it is sealed.

3. The device of claim 2, wherein said at least one port exits in said main structure on a surface of said removal tab and is connected to said mixing bladder by channel formed in the interior of said main structure.

4. The device of claim 3, wherein pressure is applied to said removal tab with a clamp to connect said at least one port to at least one connector from said external pressure source.

5. The device of claim 2, wherein said at least one port exits said main structure on an edge of said main structure and is connected to said mixing bladder by an channel formed in the interior of said main structure.

6. The device of claim 1, wherein said device is constructed of materials of low thermal mass so said device can be brought to desired temperature quickly.

7. The device of claim 1, wherein said main structure is formed of multiple layers of polymeric sheet material laminated together.

8. The device of claim 7, wherein said polymeric sheet material is degassed by exposure to a vacuum for a period of time sufficient to prevent the release of significant amounts of gases during use of the device.

9. The device of claim 7, comprising at least one layer formed of copolyester plastic.

10. The device of claim 1, wherein said gasket is formed of an adhesive material.

11. The device of claim 1, wherein said gasket is formed of an adhesive sheet material.

12. The device of claim 1, wherein said gasket is formed of a plastically deformable material.

13. The device of claim 1, wherein said gasket is formed of a resilient material.

14. The device of claim 1, wherein said gasket comprises a material selected from the group consisting of acrylic, urethane, silicone, and rubber.

15. The device of claim 1, wherein said gasket is silk-screened onto said surface of said main structure.

16. The device of claim 1, wherein said gasket is printed onto said surface of said main structure.

17. The device of claim 1, wherein said at least one port exits in said main structure on the side opposite said gasket.

18. The device of claim 1, wherein said gasket comprises multiple openings adapted to form multiple reaction chambers when said device is attached to a substrate, wherein each of said reaction chambers includes two or more mixing bladders.

19. The device of claim 1, further comprising an inlet passing through said main structure and providing fluid communication between said reaction chamber and the exterior of said main structure.

20. The device of claim 19, wherein said gasket comprises a notch aligned with said inlet such that the region of said gasket adjacent said notch supports said main structure against collapse from the pressure of a pipetting device.

21. The system of claim 19, further comprising a sealing structure for sealing said inlet selected from the group consisting of adhesive tape and a plug.

22. The device of claim 1, further comprising an outlet passing through said main structure and providing fluid communication between said reaction chamber and the exterior of said main structure.

23. The device of claim 22, wherein said gasket comprises a notch aligned with said outlet such that the region of said gasket adjacent said notch supports said main structure against collapse from the pressure of a pipetting device.

24. The device of claim 1, wherein said main structure further comprises:
    a substantially planar flexible mixing bladder layer laminated between the support layer and the diaphragm layer and comprising at least two independent openings defining the wall of the mixing bladder.

25. The device of claim 1, wherein said diaphragm layer is made of a polyester film.

26. The device of claim 1, further comprising an adhesive between a connector and the opening of one or more port.

27. The device of claim 1, further comprising a resilient sealing member positioned between a connector and the opening of one or more port.

28. The device of claim 27, wherein said connector and said opening are pressed together by a clamp.

29. The device of claim 1, further comprising a connector positioned with respect to one or more port with an alignment means.

30. The device of claim 1, wherein said main structure comprises a plurality of alternating adhesive and non-adhesive layers.

31. The device of claim 30, wherein at least one mixing bladder is defined by an opening in one said adhesive layer and bounded by two non-adhesive layers.

32. The device of claim 31, wherein said main structure further comprises at least one channel connecting said mixing bladders and said port, and wherein at least a portion of said at least one channel is defined by an opening in one said adhesive layer and bounded by two non-adhesive layers.

33. The device of claim 32, wherein said at least one channel and at least a portion of said mixing bladders are defined by openings in the same adhesive layer.

34. The device of claim 32, wherein said at least one channel and at least a portion of said mixing bladders are defined by openings in different adhesive layers.

35. The system of claim 1, further comprising:
a) at least one connector in communication with said pressure source and adapted to connect to said at least one port;
b) a base on which said substrate may be positioned;
c) an alignment means adapted to position said at least one connector in correct relationship to said at least one port to whereby said connector may be sealed to said port to provide communication between said pressure source and said mixing bladder.

36. The system of claim 1, further comprising a temperature control apparatus for maintaining said substrate, said reaction chamber forming device, and fluid within said reaction chamber at a desired temperature.

37. The system of claim 1, further comprising an alignment jig having a slot to receive said substrate, wherein placement of said reaction chamber forming device produces correct positioning of said reaction chamber forming device with respect to said substrate.

38. The system of claim 1, further comprising a brayer adapted to slide across the surface of said reaction chamber forming device, thereby pressing said reaction chamber forming device against said substrate to form an improved seal between said reaction chamber forming device and said substrate.

39. The system of claim 1, further comprising a roller adapted to roll across the surface of said reaction chamber forming device, thereby pressing said reaction chamber forming device against said substrate to form an improved seal between said reaction chamber forming device and said substrate.

40. The system of claim 1, further comprising a press adapted to apply pressure to the surface of said reaction chamber forming device, thereby pressing said reaction chamber forming device against said substrate to form an improved seal between said reaction chamber forming device and said substrate.

41. The system of claim 1, further comprising a clamp adapted to clamp said reaction chamber forming device and said substrate together.

42. The system of claim 1, further comprising a disassembly jig having a slot adapted to receive said substrate and adapted to secure said substrate while said reaction chamber forming device is peeled off of said substrate.

43. A microfluidic interface device of claim 1, wherein the reaction chamber comprises:
a) a surface of the main structure having stronger adhesive properties to said adhesive gasket relative to said substrate, such that upon removal of said device from the substrate the adhesive gasket preferentially binds to the main structure and releases from the substrate; and
b) said adhesive gasket comprised of liquid impermeable adhesive material, such that upon removal of said device from the substrate the adhesive gasket preferentially binds to the main structure and releases from the substrate;

wherein said reaction chamber forming device is adapted to adhere to a substrate to form a hybridization chamber bounded by said substrate, said lower surface, and said opening in said adhesive gasket.

44. The hybridization chamber forming device of claim 43, wherein said adhesive gasket has a thickness of about 25 µm.

* * * * *